(12) United States Patent
Haar et al.

(10) Patent No.: US 7,985,181 B2
(45) Date of Patent: Jul. 26, 2011

(54) PROCESS AND DEVICE FOR MONITORING A PATIENT

(75) Inventors: Maral Haar, Hamburg (DE); Wilfried Buschke, Lübeck (DE); Frank Franz, Lübeck (DE); Kai Kück, Hamburg (DE); Jörg-Uwe Meyer, Ratzeburg (DE); Susanne Stahlkopf, Hamburg (DE); Michael Wilkening, Lübeck (DE); Thomas Bouillon, Bern (CH); Peter Schumacher, Kirchlindach (CH); Bela Stetzer, München (DE)

(73) Assignee: Dräger Medical GmbH, Lübeck (DE)

( * ) Notice: Subject to any disclaimer, the term of this patent is extended or adjusted under 35 U.S.C. 154(b) by 904 days.

(21) Appl. No.: 11/926,715

(22) Filed: Oct. 29, 2007

(65) Prior Publication Data

US 2008/0114222 A1 May 15, 2008

(30) Foreign Application Priority Data

Nov. 14, 2006 (DE) .......................... 10 2006 053 856

(51) Int. Cl.
*A61B 5/00* (2006.01)

(52) U.S. Cl. ................... 600/301; 600/300; 128/203.14; 703/2

(58) Field of Classification Search .................. 600/300, 600/301, 544, 509, 559, 532, 302–508, 510–531, 600/533–543, 545–558, 560–595; 702/67; 715/201, 764, 828, 845, 866, 883, 700–763, 715/765–827, 829–844, 846–865; 345/581, 345/428, 619, 440, 441, 467, 418, 426, 440.1, 345/440.2, 620–689, 442–443, 156–184; 128/203.15, 203.12, 203.24, 900–916, 920–925; 514/326, 329, 731, 722, 743; 703/2–3
See application file for complete search history.

(56) References Cited

U.S. PATENT DOCUMENTS

| | | | |
|---|---|---|---|
| 5,140,519 A | 8/1992 | Friesdorf et al. | |
| 5,262,944 A * | 11/1993 | Weisner et al. | 600/300 |
| 5,473,536 A * | 12/1995 | Wimmer | 700/90 |
| 6,174,283 B1 * | 1/2001 | Nevo et al. | 600/301 |
| 6,224,549 B1 | 5/2001 | Drongelen | |
| 6,241,661 B1 * | 6/2001 | Schluess et al. | 600/300 |
| 6,956,572 B2 * | 10/2005 | Zaleski | 345/440.2 |
| 2003/0200117 A1 | 10/2003 | Manetta et al. | |
| 2003/0233257 A1 * | 12/2003 | Matian et al. | 705/3 |
| 2004/0001096 A1 * | 1/2004 | Tamura et al. | 345/771 |

(Continued)

FOREIGN PATENT DOCUMENTS

DE 38 17 052 11/1989

(Continued)

OTHER PUBLICATIONS

Syroid, N. et al. "Validation of a Remifentani Propofol Response Surface Model for Laryngoscopy", Oct. 16, 2006.*
Syroid, N. et al., "Development and evaluation of a graphical anesthesia drug display", Anesthesiology 2002; 96:565-74.*

(Continued)

*Primary Examiner* — Henry M Johnson, III
*Assistant Examiner* — Marie Archer
(74) *Attorney, Agent, or Firm* — McGlew and Tuttle, P.C.

(57) ABSTRACT

A process for monitoring a patient by a monitoring device is provided in which simplified monitoring of the patient can be carried out on the basis of a suitable selection of the parameter values and/or ranges displayed in a special manner. A suitable device (1) is provided for carrying out the process.

13 Claims, 3 Drawing Sheets

U.S. PATENT DOCUMENTS

| | | | |
|---|---|---|---|
| 2004/0059215 A1* | 3/2004 | Nishimura et al. | 600/410 |
| 2006/0081244 A1 | 4/2006 | Bouillon et al. | |
| 2006/0189851 A1* | 8/2006 | Tivig et al. | 600/300 |
| 2006/0217628 A1* | 9/2006 | Huiku | 600/544 |
| 2007/0030287 A1* | 2/2007 | Buran | 345/629 |

FOREIGN PATENT DOCUMENTS

| | | |
|---|---|---|
| DE | 10 2004 050 71 | 9/2005 |
| WO | WO 2004 030525 A2 | 4/2004 |
| WO | WO 2005038690 A2 * | 4/2005 |

OTHER PUBLICATIONS

Bouillon et al. "Pharmacodynamic Interaction between Propofol and Remifentanil Regarding Hypnosis, Tolerance of Laryngoscopy, Bispectral Index, and Electroencephalographic Approximate Entropy", Anesthesiology 2004; 100:1353-72.*

Kaul H. L. et al "Monitoring depth of Anesthesia", Indian J. Anesth. 2002; 46 (4):323-332.*

Kissin, I "Depth of Anesthesia and bispectral Index Monitoring", Anesth. Anal. 2000, 90:1114-1117.*

* cited by examiner

PROCESS AND DEVICE FOR MONITORING A PATIENT

CROSS REFERENCE TO RELATED APPLICATIONS

This application claims the benefit of priority under 35 U.S.C. §119 of German Patent Application DE 10 2006 053 856.0 filed Nov. 14, 2006, the entire contents of which are incorporated herein by reference.

FIELD OF THE INVENTION

The present invention pertains to a process for monitoring at least one parameter of a patient with the use of a monitoring means, which has at least one display means for the simultaneous display of a plurality of parameter values at different points in time, as well as to a device with a display means for the simultaneous display of a plurality of parameter values at different points in time.

BACKGROUND OF THE INVENTION

The use of monitoring means, by means of which one or more parameters of the patient are monitored, is common in the modern care for and treatment of patients, the current technical possibilities permitting the determination of a plurality of measured values over time and the display thereof by means of a display device. The physician caring for the patient being monitored or the caregiver of the patient being monitored is therefore faced with the often rather complex task of recognizing the state of monitoring of this patient at a current given point in time sufficiently, rapidly and reliably on the basis of the measured values being displayed to the physician and of identifying the actually relevant parameter values.

SUMMARY OF THE INVENTION

The object of the present invention is therefore to propose a process for monitoring at least one parameter of a patient, by means of which the above-mentioned drawback can be eliminated or at least reduced. Another object is to provide a device suitable therefor.

Thus, a process for monitoring at least one parameter of a patient with the use of a monitoring means is proposed according to the present invention, which has at least one display means for the simultaneous display of a plurality of parameter values of different points in time. "Parameter values of different points in time" is defined according to the present invention, for example, as a sequence of values of one and the same parameter measured at different points in time, e.g., of a concentration, a rate, a velocity or the like.

The process according to the present invention comprises the step of selecting at least one parameter value from the plurality of parameter values, where the at least one parameter value selected is displayed by means of the display means in a way that differs from the manner of display of the parameter values not selected from the plurality. Thus, weighing of the significance or relevance of certain parameter values is thus performed according to the present invention, which makes possible for the person monitoring the patient a more direct, more rapid and more effective access to the parameter values that are actually relevant for the monitoring from the plurality of parameter values determined on the basis of the special display of these parameter values. A first, direct, essential advantage of the present invention is therefore the increased reliability in monitoring the patient.

Since the person monitoring the patient, which person may be, for example, the anesthesiologist in charge in case of monitoring the anesthesia of the patient by means of a so-called monitor, has to deal according to the present invention only with the selected, comparatively few parameter values, the use of the process according to the present invention is less demanding in terms of attention and concentration. This enables that person to work with less fatigue and ultimately leads, in turn, to increased safety for the patient based on a less stressed caregiver or monitoring person, who will make fewer errors in estimating or evaluating the patient's status based on the selection of relevant parameter values.

The selection of certain parameter values may be performed according to clinical points of view. For example, a currently measured threshold limit value (TLV) is more relevant in case of the monitoring of anesthesia than a TLV which was measured hours before during the same anesthesia but is often still displayed in the display means. The same statement is also true of the heart rate, the respiration rate, the oxygen saturation and the like during the monitoring of a patient by means of a corresponding monitor. A selection can be made by the person skilled in the art manually or at the factory in this case as well, according to which, for example, only the last x values and/or only values that are below or exceed a predetermined parameter range, and/or only values that come correspondingly close to a certain parameter range, are selected for special display.

One possibility of displaying selected parameters in a special manner, which differs from the manner of display of non-selected parameter values, is the use of different contrasting, but with the same color. Another possibility is to use different colors. For example, signal colors may be used for selected parameter values, which require special attention of the monitoring physician or caregiver.

The special manner of display of selected parameter values may, however, also consist of displaying only the selected parameter values, whereas non-selected parameter values are not visible at all in a basic setting of the display means when the process according to the present invention is being carried out.

Such a display could be performed, independently from other features of the process according to the present invention, for example, by the function $$\text{color}(t) = (15-t)/15 \text{ for } 0 \text{ min} \leq t \leq 15 \text{ min; and}$$

$$\text{color}(t) = 0.0 \text{ for } t \geq 15 \text{ min} \quad (1)$$

in which [t]=min, 1.0 for white and 0.0 for black on a dark background. The term "color" being able to be used according to the present invention for a contrast difference between lighter and darker display, but with the same color, or for an actual color.

The present invention pertains to the use of the process according to the present invention in all monitoring stations of a patient, which are known as such to the person skilled in the art. The present invention is, moreover, also not limited to certain types of parameters. It can rather be applied to all monitored parameters.

Thus, the above-described process comprises, in a preferred embodiment according to the present invention, the selection of at least one parameter range, which is displayed in a manner of display that differs from the manner of display of the non-selected parameter range.

Provisions are therefore made according to the present invention in this embodiment for selecting ranges from the same points of view as those mentioned above, for example, clinical medical relevance, in order to make it possible to display or to display these in a manner favorable for the monitoring of the patient. Ranges within which parameter values preferably fall, which have hitherto been often indicated in the state of the art only in a linear form without clear marking of a range and/or tolerance, are displayed now in an easily detectable manner. One example of such a linear display is found in the applicant's patent DE 10 2004 050 717 B3 (corresponding to US020060081244A1), in which isoboles (lines with constant anesthesia effect parameter values) for remifentanil and propofol are shown in FIG. 4.

For example, one or more ranges between such isoboles or around an isobole, which are preferably displayed, can be selected in this embodiment of the present invention. Such isoboles indicate the probability with which a patient responds to stimuli by laryngoscopy, to shouting and to shaking at a given anesthetic concentration. These probabilities are stated as TOL and TOSS probabilities, as they will be explained below. Reference is made in this connection to the disclosure of DE 10 2004 050 717 B3. Such a range can be displayed, among other things, as described above.

It is, of course, also possible according to the present invention to select ranges other than those mentioned as examples above, between or around isoboles for special display, e.g., according to clinical points of view. For example, blood pressure and pulse limit ranges or even saturation ranges may be considered here.

The advantages of this embodiment according to the present invention correspond to those mentioned above, which will not be repeated here to avoid repetitions.

In yet another preferred embodiment of the process according to the present invention, the process comprises the step of selecting at least two or more parameter values, which are displayed differently from one another. First selected parameter values can be displayed in this embodiment in an especially distinct manner, for example, by means of an asterisk, cross, semicircle display or the like, whereas other—second, third and/or further—likewise selected parameter values, which correspond, for example, to another clinical peculiarity, are displayed in a correspondingly different manner.

This embodiment makes possible the easy-to-understand display of the selected parameters even if these are so close to one another in space in the display means that their recognition or reading by the caregiver of the patient being monitored is complicated, subject to errors and therefore associated with increased risk for the patient. This state occurs especially in the case of predicted values in monitoring situations in which there are no changes or there are only nonessential changes or deviations of the values from one another within the diagnostic period. Such a case occurs, for example, when the value predicted at 1 minute from now in the future, at 5 minutes from now in the future and at 15 minutes from now in the future are essentially one and the same value and is therefore to be displayed correspondingly "one on top of another" on the display device.

The above-described process according to the present invention is used in another preferred embodiment during the anesthesia of a patient being anaesthesized during the anesthesia. Such a monitoring with the determination of the concentrations of the anesthetics being administered, which concentrations are currently present, is disclosed, for example, in the above-mentioned DE 10 2004 050 717 B3. Reference is also made expressly here to that disclosure to the full extent. This means that the present invention can be used together in cooperation with the features of the anesthesia apparatus as it is described in DE 10 2004 050 717 B3. Moreover, it is also possible to design all the embodiments as they are disclosed in the above-mentioned patent DE 10 2004 050 717 B3 within the framework of especially preferred embodiments of the present invention with the features of each embodiment of the present invention. US020060081244A1 is hereby incorporated by reference in its entirety.

In another preferred exemplary embodiment of the process according to the present invention, this process has the step of adapting the at least one parameter range on the basis of observations, which were made during the monitoring of the patient. In practice, conventional monitoring devices have a module, which is set up to keep typical target ranges of parameters or typical response information stored. DE 10 2004 050 717 B3 also discloses such a module, which is called action module 20 there. The value ranges or value curves present in the stored form in this module and in similar modules have been regularly determined experimentally in patient or volunteer studies and analyzed by means of statistical methods to form models, as this is described in detail in paragraph [0003] of DE 10 2004 050 717 B3, to which reference is expressly made herewith. This stored information, from which it is possible to predict, for example, the point in time at which a patient will wake up from the anesthesia, is therefore always information that is "true" only "statistically" and is true for a comparatively broad population only.

Provisions are therefore made according to the present invention in this embodiment for communicating observations made in the course of the monitoring, from which the individual behavior, the individual physiology, the individual response to drug concentrations and the like of the individual patient being monitored can be inferred, to the monitoring means being used by means of a suitable input means. Based on this communicated knowledge, it is possible to output individually adapted parameter ranges and/or values, which no longer have to correspond to the parameter ranges and/or values obtained and analyzed from the patient and volunteer studies, but they may correspond to data that apply to subgroups thereof. It is therefore possible according to the present invention in this embodiment to perform a better estimation of the clinical significance of a measured parameter value and to put this into a refined and hence more accurate clinical context, for example, by adjusting upper and lower limits of a target parameter range.

Such relevant observations, which can or shall become part of the monitoring of the individual patient, are, for example, the behavior of a patient in response to a surgical incision. This may also be the observed loss or the regaining of spontaneous breathing, motion of the patient, the loss or regaining of consciousness or the like.

Such inputs may be made according to the present invention by means of a suitable touch screen, but they may also be entered via a keyboard or a mouse or the like. Provisions are also made for the automatic determination of states of the patient and automatic display of these states by means of suitable symbols.

The automatic determination of states of the patient may be accompanied by the specification of the parameter ranges on the basis of the individual patient. The states displayed in the display device, as they were described above, can be displayed by means of symbols in such a way that symbols located one on top of another also always remain recognizable for the person monitoring the patient. Provisions are therefore made according to the present invention for assigning symbols, which remain recognizable as such individually and independently from one another even when they occur simultaneously, to certain states of the patient.

The present invention pertains, furthermore, to a process for monitoring at least one parameter of a patient with the use of a monitoring means, which has at least one display means for the simultaneous display of a plurality of parameter values at different points in time in relation to stored parameter values and/or at least one stored parameter range, characterized by the step of adapting the stored parameter value and/or the at least one parameter range on the basis of observation made during the monitoring, as well as to a device suitable for carrying out this process.

The object according to the present invention is also accomplished by means of a device. All the above-described advantages, which can be accomplished by means of the process according to the present invention, can also be fully achieved with the device according to the present invention. Reference is therefore made here to the above discussion of these advantages to avoid repetitions.

In a preferred embodiment of the device according to the present invention, this device has a module for the optional display of either the selected parameter values only or of all parameter values. It is thus possible according to the present invention with the use of this device to display the reconstruction of the parameter curve in the time interval being monitored or at least all those parameter values that can be displayed by the display device at the same time. This advantageously makes possible a retrospective viewing of the particular state of the patient over the period being monitored, for example, for training purposes, documentation purposes or the like.

The present invention will be explained in more detail below on the basis of the drawings attached. Identical reference numbers designate identical components. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
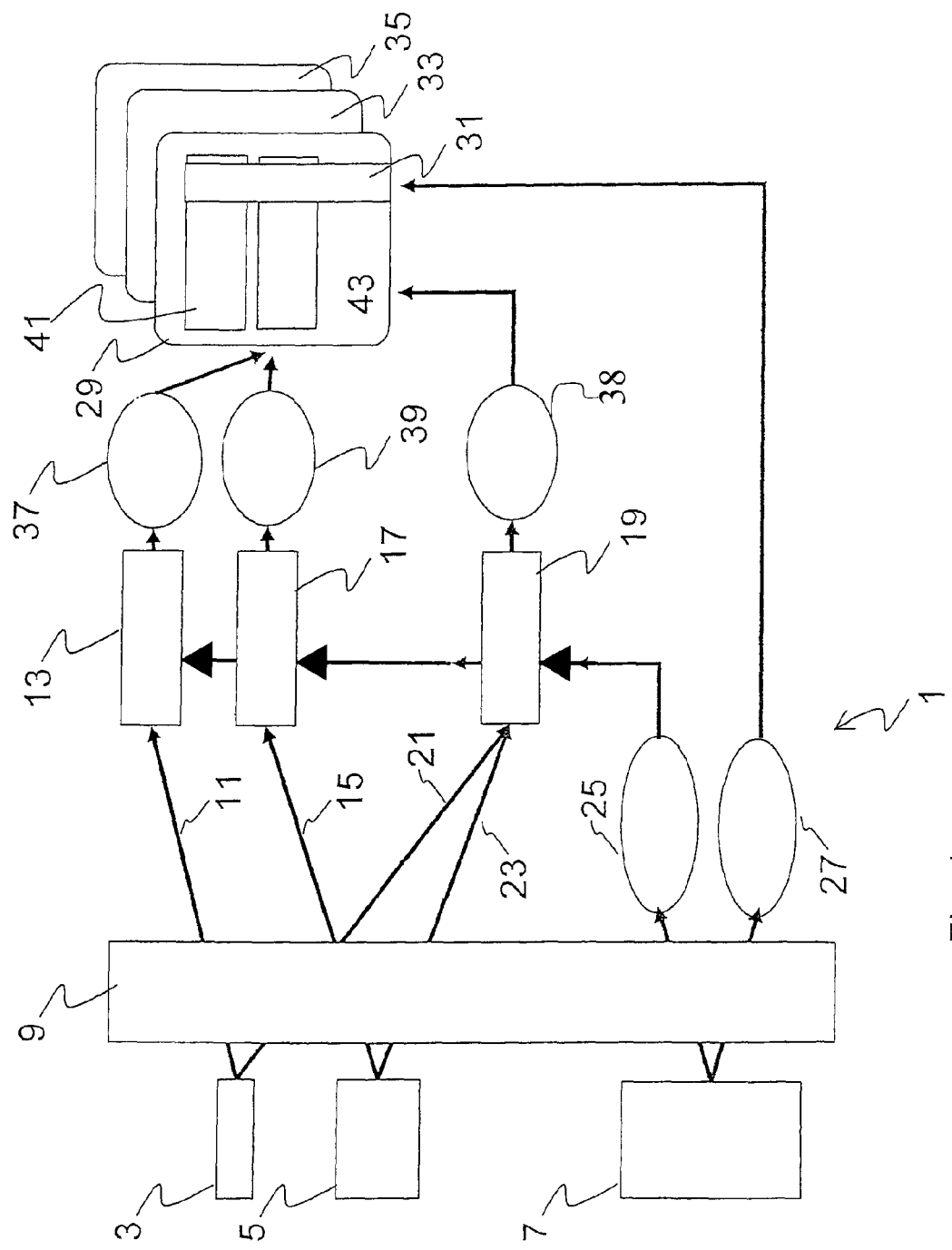
FIG. 1 is a schematically simplified view of a device according to the present invention with a display means.

Referring to the drawings in particular, FIG. 1 schematically shows, in a simplified form, a device according to the present invention for monitoring a patient. This device 1 designed, for example, as an anesthesia apparatus, and the present invention is not limited to a device for monitoring anesthesia. The device 1 has two intravenous pumps 3 and 5 for two anesthetics, and at least one of the pumps 3 and 5 may also be equipped as a means for administering a volatile anesthetic for intravenous administration. The device 1 has, furthermore, an interface 7, by means of which inputs can be made via a keyboard, mouse or the like, not shown. The device 1 has, furthermore, an information management system 9, by means of which a connection can be established between the anesthesia apparatus, a hospital information system, a network or the like for providing data that are relevant in the individual case. Data from the intravenous pumps 3, 5 as well as from the interface 7 also flow into this information management system 9. Information or data 11 on the dosage of a first anesthetic by means of pump 3 are sent in the device 1 according to the present invention as shown in FIG. 1 to a first pharmacokinetic model 13. Information or data 15 on the dosage of a second anesthetic released by pump 5 are transmitted to a second pharmacokinetic model 17. A pharmacodynamic model 19 receives information or data 21 on the name, the type or the ID of the first anesthetic being used, which is administered through pump 3, and so are comparable data 23 on the second anesthetic being administered by pump 5. The two pharmacokinetic models 13 and 17 as well as the pharmacodynamic model 19 receive, furthermore, demographic data 25 on the patient being anesthetized. These demographic data 25 can be entered via the interface 7 or are present in the stored form in the information management system 9 and can be polled. Furthermore, clinical observations 27 and other events can be transmitted for display in a display or a display means 29 via the interface 7 and/or the information management system 9. The display 29 has for this a means 31 for marking or indicating the onset of events. A memory means 33 as well as a reproduction means 35 are attached to or associated with the display 29. Calculated or predicted data 37, 39 concerning the effect time concentrations of the drugs being administered can be transmitted by means of the first pharmacokinetic model 13 and the second pharmacokinetic model 17 to the display 29 for display in a concentration-based display 41 and/or in a time-based display 43. Data 38 transmitted by the pharmacokinetic model 19 to the display 29 are used to display isoboles in display 29, as they will be explained below in reference to FIG. 2.

Figure 2:
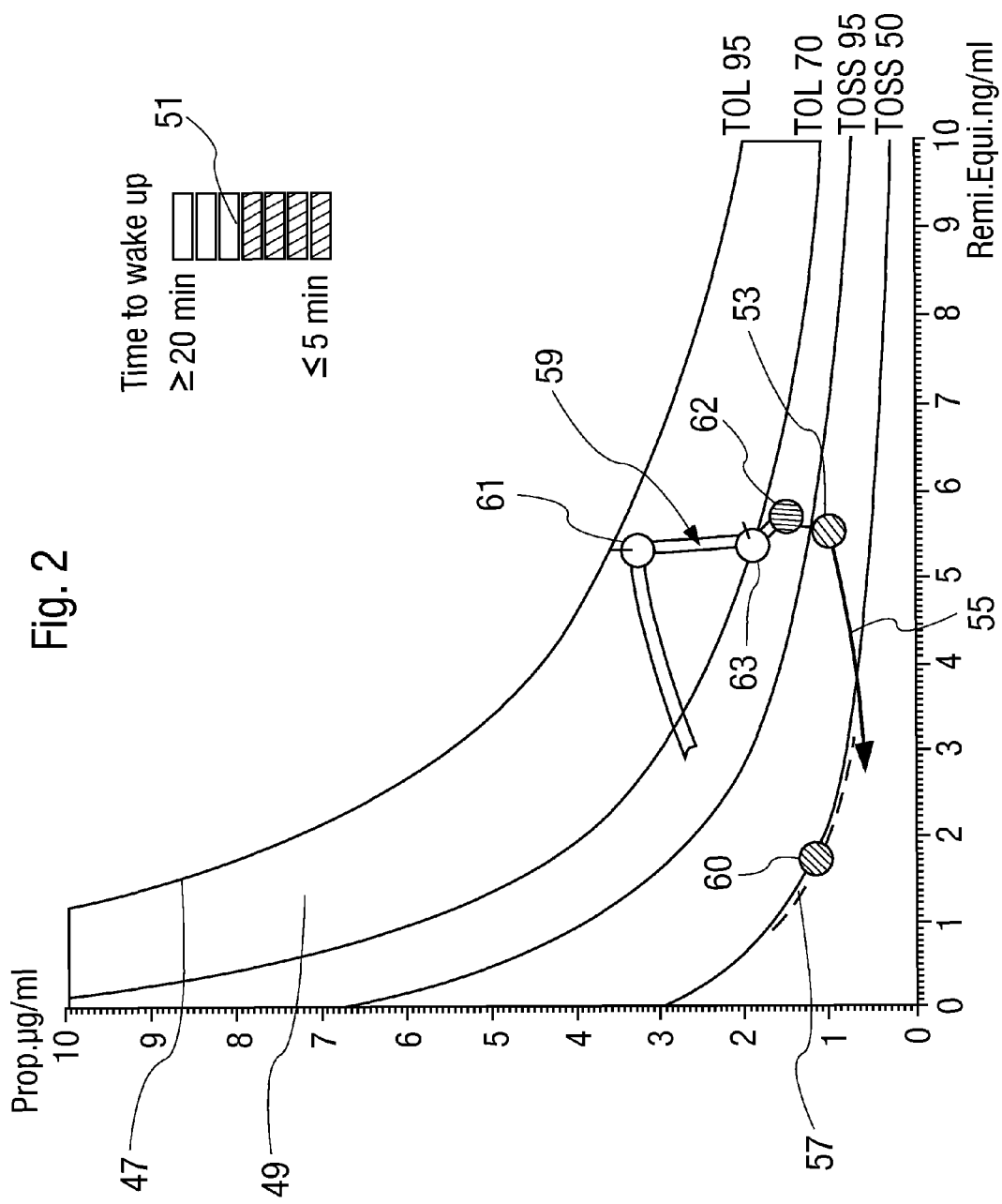
FIG. 2 is the graphic view of clinically relevant parameter values and ranges.

FIG. 2 shows the display of an effect compartment concentration of drugs, in which clinically relevant probabilities are stated, which make it possible to obtain information on whether a patient responds to certain stimuli. These stimuli for the patient include laryngoscopy, shouting and shaking. These probabilities are stated as TOL 95 and TOL 70, where TOL 95 means that 95% of all patients tolerate laryngoscopy at an administered concentration of propofol and remifentanil, whereas there is only a 70% probability that laryngoscopy is tolerated at the concentrations of propofol and remifentanil belonging to the TOL 70 isobole. The TOL 95 isobole is designated by reference number 47 in FIG. 2. A band-shaped range 49 located between the TOL 95 isobole and the TOL 70 isobole is displayed in a lighter hue compared to the background, i.e., with a contrast against the background of the image, for better recognizability by the anesthesiologist as the person monitoring the patient. The lighter image background of the band-shaped range 49 is not shown in FIG. 2 for the sake of greater clarity. This range 49 marks the range in which the patient is tolerant of pain. The view in FIG. 2 makes it possible, furthermore, on the basis of the display 51 shown in the top right part of the display window, to predict when the patient would wake up when any anesthetic administration is set and under otherwise identical conditions (ceteris paribus). This display can be shown in a so-called wake-up mode, which is based on a model-based semiquantitative estimate.

FIG. 2 also shows, furthermore, a predicted, model-based estimate of the anesthesia concentration at a 5-minute interval 53 and at a 15-minute interval 55. A broken line 57 likewise shown in FIG. 2 indicates a range of anesthesia in which 50% of normal patients with adequate analgesia wake up with sufficient respiratory drive. This line 57 corresponds to the TOSS 50 isobole, at which 50% of patients respond to shaking and to shouting. Just as line 57, the display 51 may be able to be turned on by pressing a button within the framework of a wake-up menu.

Curve or line 59 in FIG. 2 shows anesthesia concentrations present at defined points in time. It can be clearly recognized that only a few, selected parameter values of points in time in the past are shown for reasons of improving the display. It is useful to display more recent values brighter and hence highlighted, whereas "older" values become increasingly pale or darker.

FIG. 2 shows, furthermore, that clinically relevant events can be displayed by means of different symbols 60-63. As can be clearly recognized by the person skilled in the art, overlay of even events that occurred at the points in time 61 and 63 and are marked with corresponding symbols would not lead to mutual overlap in display and hence to the hiding of information, either.

Figure 3:
FIG. 3 is a view showing exemplary symbols for use in the process according to the present invention.
Figure 3:
Figure 3:
Figure 3:
Figure 3:
Figure 3:

FIG. 3 shows additional symbols 64-69, which are suitable for displaying special clinical events, such as motion of the patient, surgical incision, intubation or the like, without mutually hiding each other in case of overlap.

Thus, the present invention proposes, for the first time ever, a process for monitoring a patient by means of a monitoring means, in which simplified monitoring of the patient can take place based on a suitable selection of the parameter values and/or ranges displayed in a special manner. The present invention proposes, furthermore, a suitable device for carrying out the process according to the present invention.

While specific embodiments of the invention have been shown and described in detail to illustrate the application of the principles of the invention, it will be understood that the invention may be embodied otherwise without departing from such principles.

What is claimed is:

1. A process for monitoring at least one parameter of a patient, the process comprising the steps of:
providing a monitoring means for monitoring an anesthetic concentration of a patient undergoing anesthesia, said monitoring means has at least one display for the simultaneous display of a plurality of parameter values for an anesthetic parameter at different points in time, said display providing a set of axes and showing all of said plurality of parameter values plotted as one of a line and a set of points with respect to the axes in a same scale;
selecting at least one parameter value from the plurality of parameter values, said at least one parameter value being one of a line portion and a point of said set of points, said one of said line portion and said point having line or point characteristics different from line or point characteristics of adjacent line portions or points.

2. A process in accordance with claim 1, further comprising the step of selecting at least one parameter range which is displayed in a manner of display that differs from the manner of display of the non-selected parameter ranges.

3. A process in accordance with claim 2, wherein said step of selecting at least one parameter value includes displaying the selected parameter value with a lighter contrast and said step of selecting at least one parameter range includes displaying the selected parameter range with a lighter contrast.

4. A process in accordance with claim 1, further comprising selecting at least two parameter values, which are displayed in different manners from one another.

5. A process in accordance with claim 2, wherein the at least one parameter range is a parameter range between at least two TOL or TOSS isoboles.

6. A process in accordance with claim 2, further comprising receiving an input from an operator to modify the at least one parameter range on said display on the basis of an observation made during the monitoring.

7. A device for monitoring a parameter of a patient, the device comprising:
a monitoring device for monitoring an anesthetic concentration of a patient undergoing anesthesia, said monitoring means including a display means for the simultaneous display of a plurality of parameter values for an anesthetic parameter at different points in time, said display means showing all of said plurality of parameter values as one of a line and a set of points with respect to the axes in a continuous order; and
selecting means for selecting at least one parameter value, from the plurality of parameter values, said one parameter value being one of a line portion and a point of said set of points, said one of said line portion and said point having line or point characteristics different from line or point characteristics of adjacent line portions or points.

8. A device in accordance with claim 7, further comprising a means for selecting at least one parameter range, which is displayed in a manner of display that differs from the manner of display of the non-selected parameter ranges.

9. A device in accordance with claim 7, wherein said selecting means is for selecting at least two parameter values, which are displayed in different manners from one another.

10. A device in accordance with claim 8, further comprising input means for receiving input from an operator to modify the at least one parameter range of said display means on the basis of observation made during the monitoring.

11. A device in accordance with claim 7, further comprising an anesthesia apparatus connected to said monitoring device, said anesthesia apparatus providing said monitoring device with said plurality of parameter values, said parameter values being individual concentrations of first and second anesthetics.

12. A process for monitoring at least one parameter of a patient, the process comprising the steps of:
providing a monitoring means for monitoring an anesthetic concentration of a patient undergoing anesthesia, said monitoring means has at least one display for the simultaneous display of a plurality of parameter values of an anesthetic parameter at different points in time, said anesthetic parameter being an anesthetic action parameter formed by a concentration of first and second anesthetics, said display displaying an action diagram which plots a concentration of said first anesthetic on a first axis, and plots a concentration of said second anesthetic on a second axis, said display including a plurality of curves indicating anesthetic isoboles in said action diagram;
selecting at least one parameter range which is displayed in a manner of display that differs from the manner of display of the non-selected parameter ranges, said step of selecting at least one parameter range includes displaying the selected parameter range with a lighter contrast a range display characteristic that is different from a range display characteristic of adjacent ranges, said range being between two of said isoboles in said action diagram.

13. A device for monitoring a parameter of a patient, the device comprising:

a monitoring device for monitoring an anesthetic concentration of a patient undergoing anesthesia, said monitoring means including a display means for the simultaneous display of a plurality of parameter values of an anesthetic parameter at different points in time, said display means displaying an action diagram which plots a concentration of said first anesthetic on a first axis, and plots a concentration of said second anesthetic on a second axis, said action diagram including a plurality of curves indicating anesthetic isoboles in said action diagram; and selecting means for selecting at least one parameter range between two of said isoboles in said action diagram, said one parameter is range being displayed with a range display characteristic that is different from a range display characteristic of adjacent ranges.

* * * * *